United States Patent
Saito et al.

(10) Patent No.: US 9,708,649 B2
(45) Date of Patent: Jul. 18, 2017

(54) METHOD AND SUBSTRATE FOR NUCLEIC ACID AMPLIFICATION, AND METHOD AND APPARATUS FOR NUCLEIC ACID ANALYSIS

(71) Applicant: HITACHI HIGH-TECHNOLOGIES CORPORATION, Tokyo (JP)

(72) Inventors: Toshiro Saito, Tokyo (JP); Yoshiaki Sugimura, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 211 days.

(21) Appl. No.: 14/346,342

(22) PCT Filed: Oct. 19, 2012

(86) PCT No.: PCT/JP2012/077024
§ 371 (c)(1),
(2) Date: Mar. 21, 2014

(87) PCT Pub. No.: WO2013/065499
PCT Pub. Date: May 10, 2013

(65) Prior Publication Data
US 2014/0309120 A1  Oct. 16, 2014

(30) Foreign Application Priority Data
Oct. 31, 2011 (JP) .................... 2011-238156

(51) Int. Cl.
*C12Q 1/68* (2006.01)
*C12P 19/34* (2006.01)
*B01L 7/00* (2006.01)

(52) U.S. Cl.
CPC ............ *C12Q 1/6844* (2013.01); *B01L 7/52* (2013.01); *C12Q 1/6837* (2013.01)

(58) Field of Classification Search
None
See application file for complete search history.

(56) References Cited

U.S. PATENT DOCUMENTS

| 6,284,497 B1 * | 9/2001 | Sabanayagam ........ C07H 21/00 435/6.12 |
| 2009/0018024 A1 * | 1/2009 | Church ................ C12Q 1/6874 506/2 |
| 2009/0093373 A1 | 4/2009 | Kawaguchi et al. |
| 2011/0053150 A1 | 3/2011 | Shirai et al. |

FOREIGN PATENT DOCUMENTS

| CN | 101466847 A | 6/2009 |
| CN | 101835905 A | 9/2010 |
| JP | 2002-525125 A | 8/2002 |
| JP | 2009-500004 A | 1/2009 |
| JP | 2011-520420 A | 7/2011 |

OTHER PUBLICATIONS

Chinese Office Action received in corresponding Chinese Application No. 201280052238.8 dated Oct. 30, 2014.
Adessi et al., "Solid phase DNA amplification: characterisation of primer attachment and amplification mechanisms", Nucleic Acids Research, 2000, vol. 28, No. 20, e87.
Shendure et al., "Accurate Multiplex Polony Sequencing of an Evolved Bacterial Genome", Science, Sep. 9, 2005, vol. 309, pp. 1728-1732.
Anderson et al., "Fluorescent Structural DNA Nanoballs Functionalized with Phosphate-Linked Nucleotide Triphosphates", Nano Letters, 2010, vol. 10, pp. 788-792.
Ju et al., "Four-color DNA sequencing by synthesis using cleavable fluorescent nucleotide reversible terminators", Proceedings of the National Academy of Science of the United States of America, Dec. 26, 2006, vol. 103, No. 52, pp. 19635-19640.

* cited by examiner

*Primary Examiner* — David Thomas
(74) *Attorney, Agent, or Firm* — Mattingly & Malur, PC

(57) ABSTRACT

The present invention relates to a method for nucleic acid amplification, which enables clusters of amplified nucleic acid fragments to be sequenced by a sequencer to be formed at a high density and improves throughput of nucleic acid sequence analysis by amplifying the number of nucleic acids in the cluster to 10,000 molecules or more; and a method for nucleic acid amplification for enhancing read accuracy, which achieves a high cluster density and increases the number of the amplified fragments in the cluster by the steps of previously forming a pattern of primer DNAs on a base material and fixing bulky template DNA molecules synthesized from DNA samples thereon to induce amplification reaction.

14 Claims, 4 Drawing Sheets

METHOD AND SUBSTRATE FOR NUCLEIC ACID AMPLIFICATION, AND METHOD AND APPARATUS FOR NUCLEIC ACID ANALYSIS

TECHNICAL FIELD

The instant application contains a Sequence Listing which has been submitted electronically in ASCII format and is hereby incorporated by reference in its entirety. Said ASCII copy, created on Feb. 23, 2016, is named H-9191_SL.txt and is 2,102 bytes in size.

The present invention relates to a nucleic acid amplification method, a nucleic substrate, and an apparatus for nucleic acid analysis, which are used for analysis of nucleic-acid base sequences.

BACKGROUND ART

In recent years, new techniques for DNA and RNA sequencing have been developed. Conventionally, methods using electrophoresis have been used for DNA and RNA sequencing, which involve the steps of: preparing cDNA fragment samples, which are synthesized from cDNA fragments or RNA fragments for sequencing through reverse transaction reaction; inducing dideoxy reaction by a known Sanger method; and measuring molecular weight separation development patterns by electrophoresis for analysis.

In contrast to this, recently, methods, which enable a plurality of DNA fragment samples to be fixed on a substrate to acquire sequencing information in parallel, have been developed, improving remarkably analysis speed of bases. These techniques enable a plurality of samples to be analyzed in parallel by arranging a cluster of amplified nucleic acid sequences to be analyzed on a plate to measure using two-dimensional image sensor. For example, a nonpatent literature 1 discloses a technique, which involves the step of inducing PCR reaction using a primer fixed on the substrate to form a cluster of an amplified gene fragments on the substrate. Moreover, a nonpatent literature 2 discloses a technique, which involves the steps of inducing emulsion PCR reaction to amplify and fix the nucleic acid sequences on the surfaces of microparticles and fixing the microparticles on the plate.

For these super-parallel sequencer, the formation of a cluster is an important step because the formation of a high-density cluster increases sequencing information, which can be acquired from an image sensor at a time, while an increase in the number of gene fragments per cluster achieves the enhancement of signal intensify, improvement in reliability of sequencing information, and simplification of a detector.

CITATION LIST

Patent Literature

Patent Literature 1: Japanese Unexamined Patent Application Publication (Translation of PCT Application) No. 2002-525125
Patent Literature 2: Japanese Unexamined Patent Application Publication (Translation of PCT Application) No. 2011-520420 Nonpatent Literature
Nonpatent Literature 1: Nucleic Acids Research, 2000, vol. 28, No. 20, e87.
Nonpatent Literature 2: Science 2005, vol. 309, pp. 1728-1732.
Nonpatent Literature 3: Nano Letter 2010, vol. 10, pp. 788-792.
Nonpatent Literature 4: P. N. A. S. 2006, vol. 103, pp. 19635-19640.

SUMMARY OF INVENTION

Technical Problem

The super parallel sequencer detects fluorescent reaction or luminescent reaction emitted from the amplified gene cluster arrayed on the plate from a two-dimensional image sensor to the sequencing information on individual gene fragments. Accordingly, with higher-density amplified gene cluster, an increased amount of sequencing information may be acquired, achieving higher throughput.

A conventional method for forming a plurality of clusters through amplification reaction on the substrate involves the step of randomly applying DNA samples as templates on the substrate to induce amplification reaction using the primer previously fixed on the substrate as a starting point, as disclosed in the Patent Literature 1. This method involving the step of randomly applying template DNA on the substrate has a limitation that percentage of the partitions, in which only one molecule of template DNA is applied, may be at most about 37% because with an increase in cluster density, the frequency distribution of the number of template DNA molecules applied in a given area of partition is Poisson distribution. For this reason, assuming that one molecule be applied in the individual partitions of an average 500 nm square, each, on the substrate, ideally, the cluster density of 4 million clusters/mm$^2$ may be achieved; however, this method has a limitation that even though the concentration of template DNA is optimized as much as possible, actually, only the cluster density of 1.3 million clusters/mm$^2$, equivalent to about one third of the ideal cluster density, may be achieved. In other words, the method has such a problem to be solved that: fixation of the template DNA samples at a high concentration causes several types of DNA molecules to be amplified in one partition because template DNA molecules are closely fixed on the substrate, making it impossible to perform adequate sequence analysis; on the other hand, fixation of DNA samples are fixed at a low concentration decrease the cluster density, deteriorating the throughput.

The Patent Literature 2 discloses a method involving the steps of inducing amplification reaction and fixing the products yielded from amplification (hereinafter, simply referred to as the amplified products) on a fixation pad, which has been previously formed on the substrate. However, in this method, Rolling Cycle Amplification (RCA) is used as amplification reaction, making it difficult to achieve an amplification factor as high as more than ten 10,000-fold. Since analysis with high throughput requires fast detection of fluorescent spots, the number of DNA fragments per cluster is preferably high; while, it is difficult to achieve the amplification factor as high as more than 10,000-fold in terms of the rate of DNA synthesis reaction only by inducing RCA reaction for several hours, which is suitable for practical use.

The present invention may provide the method, which achieves the cluster density higher than that expected from the rate of the Poisson distribution and amplifies the number of DNA fragments in each of the clusters to 10,000 molecules or more, enabling easy detection.

Solution to Problem

The inventors of the present invention had earnestly made a study and successfully develop amplification method, which achieves both of the cluster density higher than that obtained from Poisson distribution and the amplification factor for the number of DNA fragments in the cluster equal to or higher than 10,000 molecules.

Specifically, the nucleic acid amplification method was developed, which enables the number of DNA fragments in each of clusters to be amplified to 10,000 molecules or more at a cluster density higher than 1.3 million/mm$^2$, which is obtained from the Poisson distribution, assuming that, in particular, a square of 500 nm on a side be one partition for clusters.

This method involves the steps of forming isolated regions, in which primers are fixed at a high density on the substrate at a high density and applying template DNA molecules to be amplified in the region one by one. Application of the molecules larger than or equal to, in physical size, the fixation region enables template DNA molecules to be applied in each of the fixation regions one by one. More specifically, for example, macromolecules are synthesized for each template DNA through RCA reaction and then applied in each of fixation regions with primer DNA previously fixed thereto to achieve single molecule application. After single molecule application, through amplification reaction, for example the RCA reaction, the amplified products yield in the primer fixation region using the primer as a starting point fixed on a base material. Since the individual products yielded from the RCA reaction contain only one type of base sequence of template DNA, instead of macromolecules, only one type of products from amplification may be synthesized in the individual primer fixation regions. Thus, the substrate for amplified products, which are capable of being well applicable to subsequent sequence reactions, may be fabricated.

Advantageous Effects of Invention

The present invention may achieve the cluster density higher than expected from the rate of the Poisson distribution, which cannot be achieved by the conventional method for randomly fixing DNA samples on the substrate; amplify the number of DNA fragment in each of the clusters to 10,000 molecules or more to increase the number of DNA fragments for sequence analysis per field of vision; in addition; and enables sequence analysis to be performed with high throughput because of its shorter exposure time necessary for detection.

DESCRIPTION OF EMBODIMENTS

Figure 1:
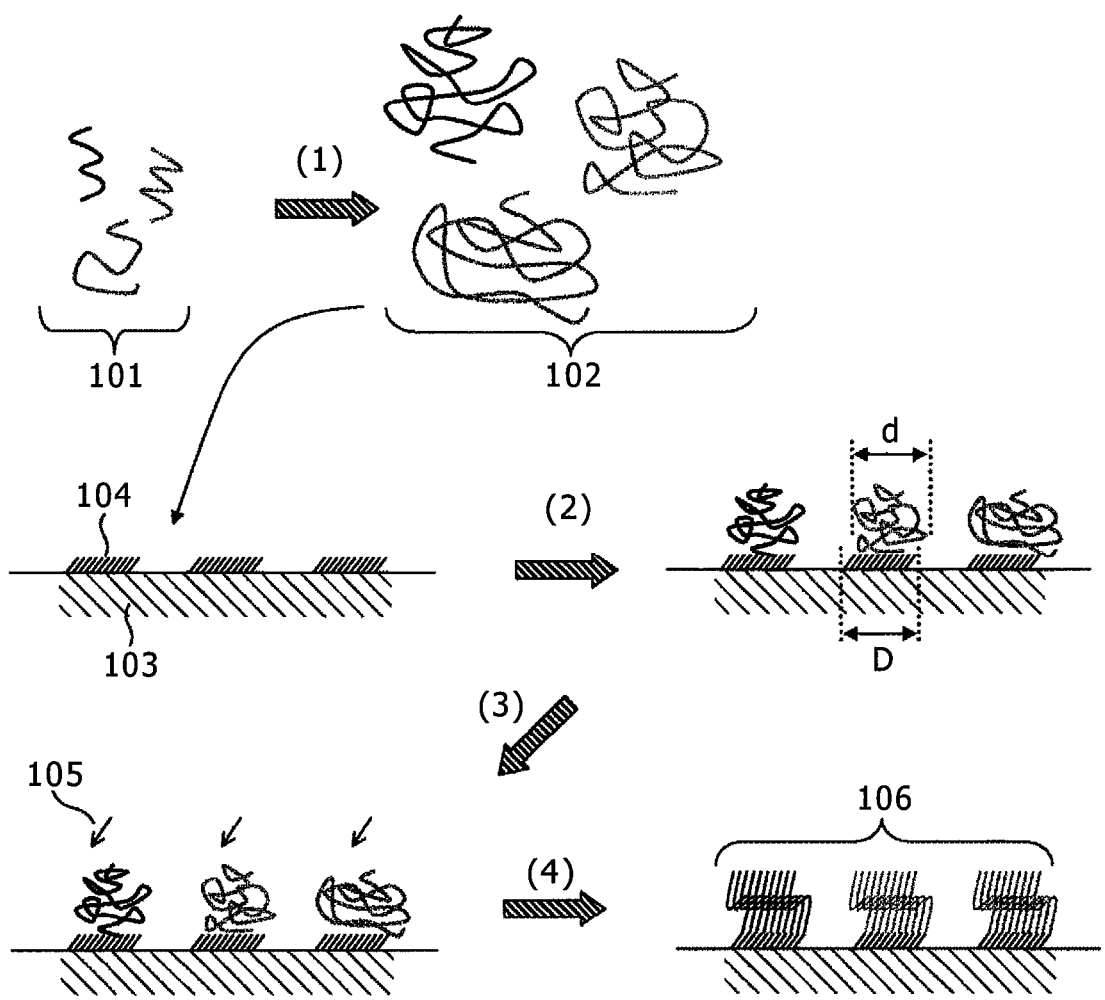
FIG. 1 is a view explaining an example of the mechanism for a gene amplification method of the present invention.

By reference to examples of the present invention, a method for nucleic acid amplification is disclosed, which involves the steps of: arranging the regions with first nucleic acid fragments fixed therein and the regions with no first nucleic acid fragments fixed therein on the surface of a base material; fixing second nucleic acid fragments having at least two or more base sequences to be analyzed on the same chain in the region with the first nucleic acid fragments fixed therein; applying third nucleic acid fragments to induce amplification reaction on the second nucleic acid fragments using first and third nucleic acid fragments as primers.

Moreover, by reference to the examples of the present invention, the method for nucleic acid amplification is disclosed, which is characterized in that the average value for the diameters of second nucleic acid fragments are larger than one-half of the average value for the diameters of the regions with the first nucleic acid fragments fixed therein.

In addition, by reference to the examples of the present invention, the method for nucleic acid amplification is disclosed, which is characterized in that the second nucleic acid fragments are single-stranded and have a self-annealing structure.

Furthermore, by reference to the examples of the present invention, the method for nucleic acid amplification is disclosed, which is characterized in that it involves a step of removing a complementary strand of the products from extension reaction on the first nucleic acid fragments after the amplification reaction.

Moreover, by reference to the examples of the present invention, the method for nucleic acid amplification is disclosed, which is characterized in that the second nucleic acid fragments are the products from the extension reaction with strand displacement reaction in the presence of polymerase having strand displacement activity using circular nucleic acid fragments having the base sequence to be analyzed as a template.

Additionally, by reference to the examples of the present invention, the method for nucleic acid amplification is disclosed, which is characterized in that the amplification reaction is an isothermal reaction.

Furthermore, by reference to the examples, a substrate for nucleic acid amplification is disclosed, which is characterized in that the average value for the diameters of the regions, in which nucleic acid fragments having a base sequence to be analyzed are fixed on the substrate for nucleic acid amplification and the average value for the diameters of the regions with the nucleic acid fragments fixed therein is equal to or lower than 500 nm and the average value for the numbers of nucleic acid fragments in the regions with the nucleic acid fragments fixed therein is equal to or more than 10,000 molecules.

Moreover, by reference to the examples of the present invention, a substrate for nucleic acid amplification for the nucleic acid amplification, which has at least one flow channel, is disclosed.

Additionally, by reference to the examples, an apparatus for the nucleic acid amplification, which has at least one thermoregulator and one solution sending mechanism, is disclosed.

Thereinafter, the above-mentioned and other novel characteristics and effects of the present invention are described by reference to accompanying drawings. Herein, for the reader to well understand the present invention, particular embodiments are described in detail but the present invention is not limited to these descriptions.

Example 1

By reference to an example 1, the method for nucleic acid amplification of the present invention is described using FIG. 1. Bulky DNA molecules 102 are synthesized from a DNA sample 101 (1). It is required that the individual bulky DNA molecules 102 retain the information on base sequence of the DNA sample 101, from which the DNA molecules 102 are derived, with no confusion. To satisfy the above requirement, Rolling Circle Amplification (RCA) reaction may be used. RCA reaction is described in detail by reference to the example 3. On the other hand, on the surface of a base material 103, DNA molecules 104 as primers are fixed into a pattern in advance. A method for fixing the primer DNA 104 into a pattern is disclosed by reference to an example 2. The bulky DNA molecules 102 are hybridized in the regions, in which the primer DNA molecules 104, for fixation (2). To achieve this, a complementary sequence of the base sequence, which is part of the bulky DNA molecule 102, is inserted in the primer DNA 104 in advance. The primer DNA 104 may only have the same base sequence in the individual fixation regions; accordingly, a common base sequence may only be inserted in the bulky DNA molecule 102 so as to have its complementary sequence.

It is required that different types of DNA samples 101 are applied to the fixation regions for the individual primer DNA 104 one by one. It was discovered that two or more bulky DNA are not fixed in the fixation region provided that the condition d>D/2 is satisfied, assuming that the diameter of the fixation region be D and the diameter of the bulky DNA 102 be d; namely, only one type of DNA samples 101 are applied, successfully achieving the present invention. Provided that the condition d>D/2 is satisfied, another bulky DNA is never physically fixed in the regions with the bulky DNA 102 fixed therein; hence, since the Poisson distribution condition derived from a repeated independent event is not satisfied, the rate of single molecule fixation equal to or higher than about 37% of single molecule fixation expected from the rate of the Poisson distribution may be achieved. Even though the concentration of the bulky DNA 102 is increased to react with the base material 103, two or more DNA 102 is never fixed in one fixation region; hence, for example the single molecule fixation rate may be achieved as high as about 70% or more equivalent to about two times the limit value of the Poisson distribution.

Next, the base material is immerged in an aqueous solution containing DNA synthetase and a substrate for four types of bases, extension reaction is induced on the primer DNA 104 using the bulky DNA molecules 102 as the templates for double-stranded DNA synthesis (3). The complementary strand synthesis (3) using the bulky DNA molecules 102 as the templates may be completed by reaction at a constant temperature of about 37° C. for about 10 minutes depending on the type of polymerase to be used. Then, primer DNA 105, of which orientation is opposite of that of the primer DNA 104, are applied to induce OCR reaction (4). If during PCR reaction, they are denatured in normal temperature cycle at the normal temperature of 95° C., the bulky template DNA molecules 102 would detach from the substrate, leading to failure of desired amplification. To address this problem, preferably the PCR reaction is induced at a constant temperature so that the primer DNA 104 may be annealed and then the complementary strand synthesis reaction is induced when the double-strand is partially cleaved. The result of earnest discussion about reactive conditions revealed that the factors, which get control over amplification efficiency, are the reaction time and primer concentration. At the reaction temperature of 70° C. or higher, the bulky DNA molecules 102 are detached, deteriorating the amplification efficiency. On the other hand, at the reaction temperature of 50° C. or lower, the amplification factor was low and even though the reaction was proceeded over three hours, the amplification factor did not reach 10,000-fold. For this reason, it was demonstrated that the reaction temperature is preferably between 50 to 70° C., and more preferably about 60° C. Next, the correlation between the density and amplification factor of the primer DNA 104 were earnestly discussed. The result showed that even though the reaction is proceeded over three-hour reaction, the amplification factor does not reach 10,000-fold with no fixation density of about 50,000 molecules/$\mu m^2$ (to single molecule/square of 4.5 nm on a side). For this reason, the fixation density of primer DNA 104 is preferably 10,000 molecules/$\mu m^2$ or more, and more preferably 100,000 molecules/$\mu m^2$ or more. At about 0.1 to 0.5 $\mu M$, equivalent to that for the PCR reaction in a normal solution, of primer DNA 105 concentration, sufficient amplification was achieved. The polymerase has preferably strand replacement activity and any of Phi29, Bst polymerase, Csa polymerase, 96-7 polymerase and the like may be used. After the PCR reaction, a double-strand composed of the product from the extension reaction on the primer DNA 104, which were previously fixed on the base material 103, and the product from the extension reaction on the primer DNA 105 is formed on the base material 103. To proceed efficiently the sequence reaction on the products from the extension reaction for base sequence analysis, it is preferable that the product from the extension reaction on the primer DNA 105 is removed to leave single strand behind. Denaturation through high-temperature treatment, which is most convenient, preferably at 70° C. or higher and more preferably at 90° C. or higher for about two minutes enables single-strand to be formed sufficient for sequence reaction.

As described by reference to the example 1, according to the method of the present invention, the cluster density, namely fixation region density depends on the fixation region density for the primer DNAs 104, accordingly, different types of DNA samples 101 may be applied to the individual fixation regions at a high fixation density one by one independently of the Poisson distribution. For example, if the fixation region is formed into 500 nm square, a high cluster density of 2 million molecules/$mm^2$ or higher may be achieved. On the other hand, the DNA density in the cluster is determined depending on the amplification factor and the area per cluster. For example, for the fixation region (cluster formation region) of 500 nm in diameter with 50,000 molecules/$\mu m^2$ or more in primer DNA density, the amplification factor may reach about 10,000-fold in the reaction time of three hours, achieving 10,000 molecules/cluster.

Example 2

Figure 2:
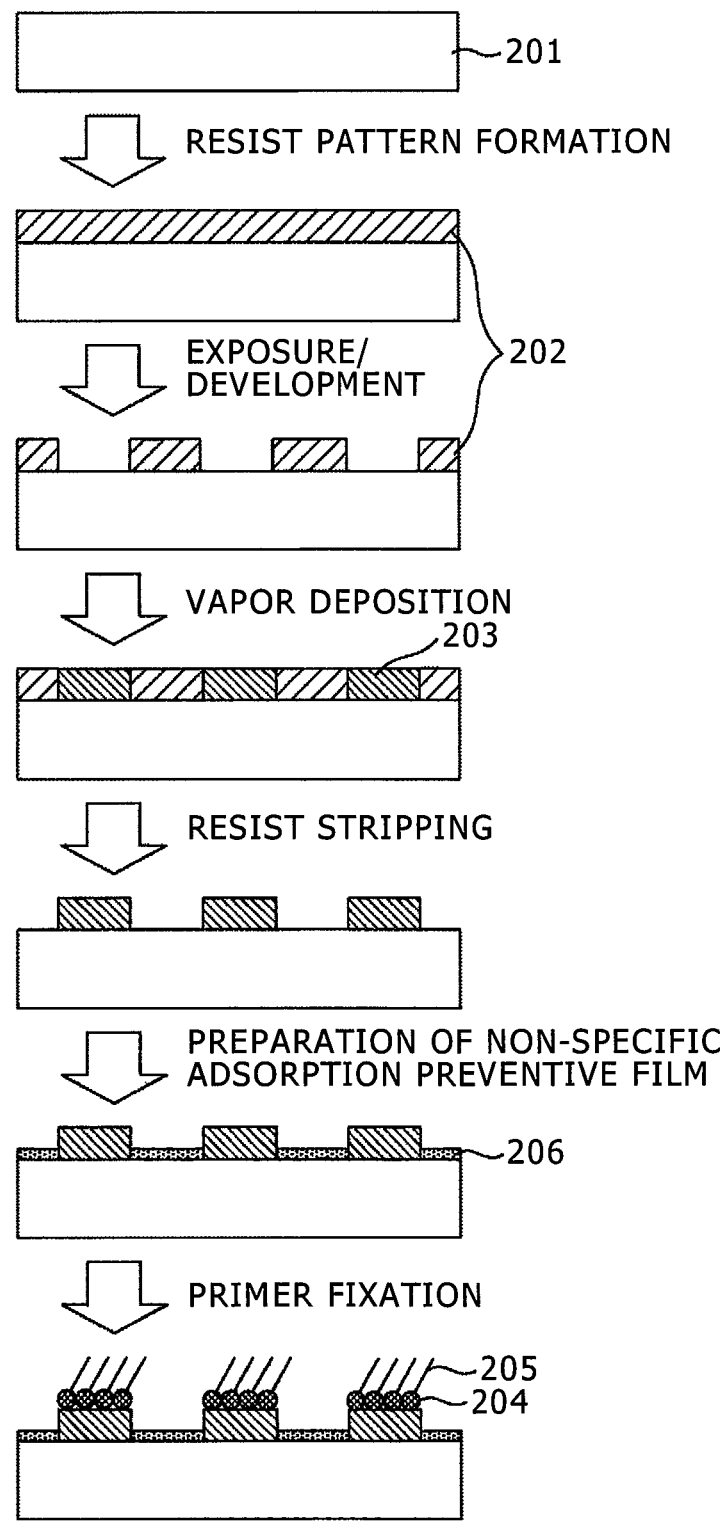
FIG. 2 is a view explaining an example of the method of fabricating a substrate used for the gene amplification method of the present invention.

By reference to an example 2, a preferred example of a technique is described for fixing the primer DNAs on the base material used by the method for nucleic acid amplification of the present invention using FIG. 2.

Positive photoresist for electron beam 202 is applied on a smooth support base material 201 by the spin coat method. For the smooth support base material, any of glass substrates, sapphire substrates, silicon wafer and the like may be used. For the substrate for nucleic acid amplification, which requires irradiation of excitation light from the rear side, which is opposed to the plate in which the nucleic acid fragments have been fixed, a quartz substrate or sapphire substrate, both of which have superior light transmissibility may be used. The positive photoresisters for electron beam include, for example, polymethylmethacrylate and ZEP-520A (Zeon Corporation). Alignment is performed using marker positions on the substrate and then electron beam lithography is applied to form through-holes into the photoresist. For example, the through-holes with 200 nm in diameter are formed. Considering manufacturing convenience and yield ratio, as well as the number of nucleic acid fragments, which may be analyzed in parallel, formation of through-holes at the intervals of about 0.5 µm is suitable depending on the number of nucleic acid fragments, which may be analyzed in parallel. The size of the through-hole formation region also depends on the number of the nucleic acid fragments, which may be analyzed in parallel, as well as largely on the accuracy of position detection and position resolution in a detector. For example, summing that the primer DNA fixation regions be formed at the intervals of 0.5 µm, 4 million clusters may be formed within a square of 1 mm on a side. After through-hole formation, a film layer of a material for an adhesive pad 203, for example gold, is deposited by sputtering. When a glass substrate or sapphire substrate is used for the smooth support base material and gold is used as the adhesive pad material, a titanium or chrome thin film is preferably inserted between the substrate material and the adhesive pad material to reinforce adhesion power between them. After the photoresist is detached, non-specific adsorption preventive treatment is applied on the surface of the smooth substrate excluding the portions with the adhesive pad 203 formed. To achieve adsorption prevention on fluorochrome-labeled nucleotides, the substrate is coated with molecules with negatively-charged functional groups. For example, epoxy silane is coated on the surface of the substrate by spin-coat technique, heat-treated, and treated with a weak acid solution (about pH5 to pH6) to open the epoxy group so as to introduce an OH group on the surface of the substrate, achieving non-specific adsorption preventive effects.

It is preferable that a primer DNA 205 is previously modified with a functional group 204. When gold is used as the adhesive pad material, a thiol group may be used as the functional group 204. The base material with the adhesive pad 203 is immersed in the primer DNA 205 aqueous solution containing the functional group 204, taken out from the solution after a given reaction time passes, excessive solution is rinsed away with water, and the substrate is dried to fabricate the substrate for nucleic acid amplification, which has a pattern of the primer DNAs fixed thereon. By reference to the example 2, an example of the method for fabricating the substrate for nucleic acid amplification using the electron beam exposure device; moreover, the use of a photoexposure device also makes it possible to fabricate the substrate for nucleic acid amplification in just the same manner as that for the electron beam exposure device.

Furthermore, besides the above-mentioned lithography techniques, the use of other techniques, such as nanoimprinting and contact-printing, makes it possible to form the adhesive acid pattern. Additionally, by forming a phase-separated microstructure using a block copolymer bridging between polymer molecules with different compatibilities and dissolving one of these two different phase polymer molecules is dissolved to form a concave pattern, a metal pad pattern may be formed using the concave pattern as a template.

Example 3

Figure 3:
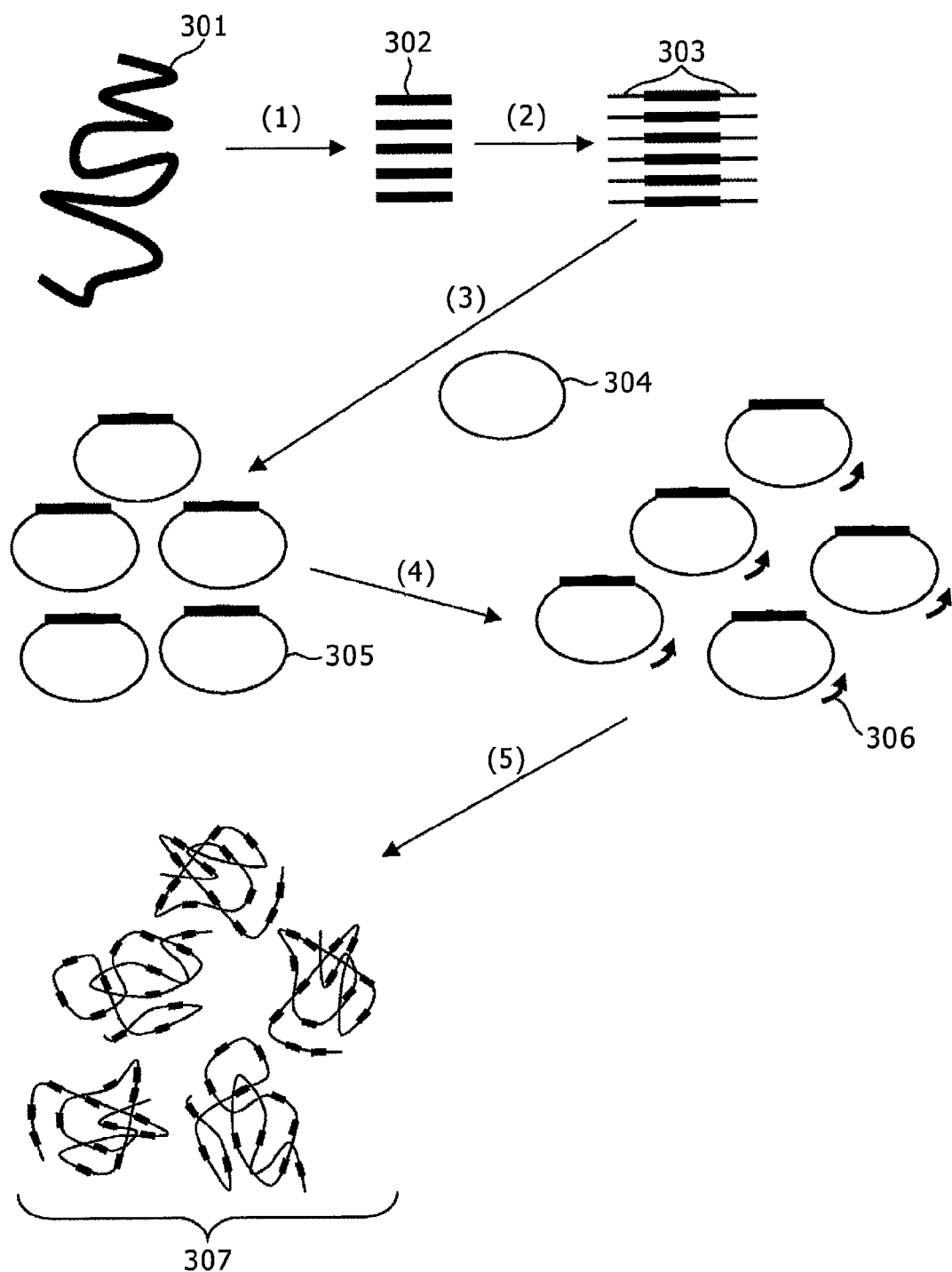
FIG. 3 is a view of an example of the method of forming bulky template DNA used for the gene amplification method of the present invention.

By reference to an example 3, an preferred example of the method for producing bulky DNA molecules from DNA samples, which are used in the method for nucleic acid amplification of the present invention, is described using FIG. 3.

The DNA samples 301 are fragmented by any of common practices, such as enzyme digestion, shear decomposition, and sonication (1). The base length of a fragment 302 is preferably between 50 to 2000 bases, and more preferably between 100 to 500 bases. Since the fragment 302 is coupled to a linker DNA in the successive step to form a circular DNA and DNA synthesis is induced, too long fragment length may cause the bulky DNA structure to deviate from the desired shape. On the other hand, too short fragment length may create concern about failure of the amplification factor to reach the desired value. It is preferable that the fragment length is determined considering the above-mentioned conditions, and that the method for DNA fragmentation (1) is selected, which enables the most suitable fragment length to be achieved.

It is preferable that both ends of the fragment 302 are smoothed and then an adaptor 303 is ligated at each of these smoothed ends (2). Smoothing may be achieved by a method, which fills overall an overhang sequence at the 5' single strand with polymerase and dNTPs, or a method, which removes an overhang sequence at the 3' single strand with polymerase having 3' exonuclease activity. To avoid mutual ligation between the fragments, it is preferable that a 3' phosphate group is previously replaced by a hydroxyl group using, for example using 3' phosphatase activity of T4 kinase. By adding the adaptors 303 to all the fragments 302 through ligation so as to couple to the linkers 304 for form a ring, circular DNAs 305 may easily be synthesized (3). Plasmid DNA may be used for the linker 304 to form the circular DNA. For example, the multi-cloning site is cut in the presence of an appropriate enzyme and the fragment 302 with the adaptor 303 added is incorporated therein. The incorporated plasmid may be amplified through transformation of *Bacterium coli*. Next, a primer DNA 306 is hybridized with the circular DNA 305 (4) and RCA reaction is induced using polymerase having strand replacement activity (5). Polymerases, which may be used for RCA reaction, include phi29 polymerase, Bst polymerase, Csa polymerase, and 96-7 polymerase. Since these polymerases are different in optimal reaction temperature and condition, any of them may be selected appropriately depending on the Tm value of the primer sequence to be hybridized. To control the size of a RCA product 307, the reaction time and temperature need to be controlled and polymerase should be selected. Moreover, as disclosed in, for example the nonpatent literature 3, by previously incorporating a base sequence having a self-loop structure, in the linker 304 to form the circular DNA, the RCA product 307 may be controlled so as to have a spherical shape. Furthermore, the use of a palindromic sequence having a palindrome structure as the base sequence having the self-loop structure is useful. Additionally, the self-loop structure, called an aptamer, may be used. When the above-mentioned base sequence having a high-order structure through self-hybridization is incorporated in the linker 304, a long single-strand RCA product 307 has a periodically-constricted structure, finally being formed into a spherical shape. Unlike an indefinite shape taken by the RCA product, the spherical shape taken by the RCA product makes it possible to easily control the size of the template DNA (RCA product) to fit the area of the fixation region. The nonpatent literature 3 discloses the method for synthesizing spherical DNAs with 50 to 150 nm in diameter.

The inventors of the present invention incorporated the aptamer structures of 10 to 20 base length in the plasmid of 500 base length (sequence: 1) and then reacted suing Csa polymerase for three hours to acquire the RCA product of 100 to 200 nm in diameter. An oligo DNA with the terminal modified with thiol (sequence: 2) was fixed as the primer on the gold pad substrate of 100 nm in diameter and 0.5 µm in interval between pads deposited on a quartz substrate using the electron beam lithography described by reference to the example 2. The gold pad substrate was immersed in a reaction solution containing given amounts of the RCA products, Csa polymerase, inverted primers (sequence: 3), and dNTPs, then, incubation was performed at 37° C. for 10 minutes to synthesize a complementary strand, and then amplification reaction was performed at an increased temperature of 60° C. for three hours. After unreacted components were rinsed with water, a fluorescent probe DNA having the synthesized DNA complementary strand, of which end was Cy3-labeled (sequence: 4), was hybridized to the substrate and the substrate was observed under a fluorescent microscope; amplified products were synthesized on the gold pads. The ratio of the gold pads, on which the amplified products were observed, was about 70%. For this reason, it was verified that the cluster density of about 2.8 million clusters/mm$^2$ may be achieved. Moreover, it was determined that with regard to the number of DNA molecules per pad, based on the comparison of fluorescent intensity with that of fluorescent beads, which have unknown numbers of fluorescent molecules, as described by reference to the example 4, DNA molecules were synthesized at the density of at least about 10,000 DNA molecules/cluster/pad. Accordingly, it was demonstrated that the DNA fragment density of about 10,000 DNA molecules/cluster might be achieved.

As known from the above-mentioned examples, it is clarified that the high cluster density and the high density of DNA fragments per cluster may be achieved by synthesizing bulky DNAs as template DNAs through any of reactions such as RCA reaction and fixing the bulky template DNAs, for amplification, on the base material, which is previously fixed in the regions, were the primers are isolated.

Example 4

Figure 4:
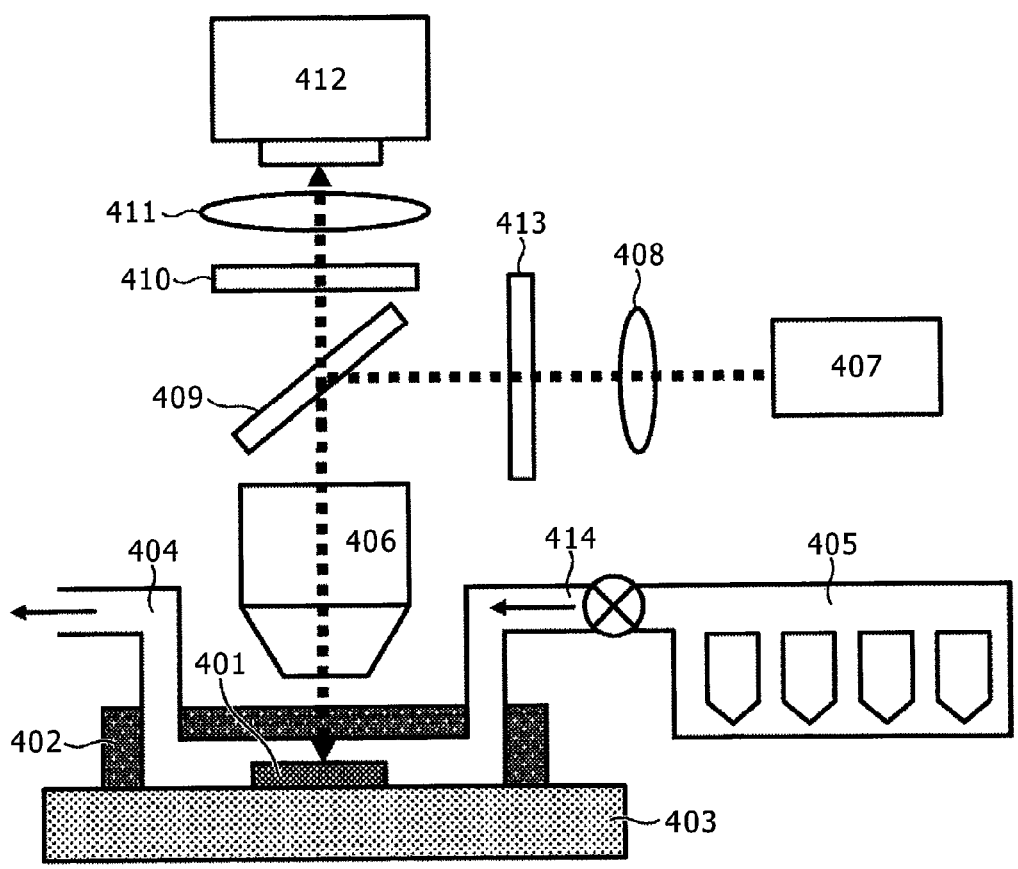
FIG. 4 is a view of an example of the configuration of an apparatus for inducing sequence reaction using the clusters of amplified gene fragments prepared according to the present invention.

By reference to an example 4, an example of the preferred configuration of an apparatus for nucleic acid analysis using the substrate for nucleic acid amplification of the present invention using FIG. 4.

The apparatus for nucleic acid analysis according to the example 4 of the present invention has the parts for: applying an aqueous solution of bulky DNA molecules, washings, a nucleic acid synthetase solution, and a solution of fluorescently-labelled base material (dNTP) on the substrate for nucleic acid amplification, on which a plurality of isolated micro regions are formed on the surface thereof for fixing the nucleic acid fragments; regulating the temperature for controlling the amplification response of the bulky template DNA molecules; irradiating light onto the substrate for nucleic acid amplification; and measuring luminescence on the fluorescently-labeled base material. More specifically, a substrate for nucleic acid amplification 401 is placed on a thermoregulating plate 403 and a flow channel formation member 402 with a flow channel 404 formed therein is adhered on the plate 403 to form a reaction chamber. PDMS (Polydimethylsiloxane) may be used for the flow channel formation member 402. A solution sending unit 405 is connected to an inlet 714, and all the chemical solutions required for reactions and rinsing are stored in the solution sending unit 405.

The aqueous solution of bulky template DNA molecules, the solution of substrate for nucleic acid synthesis (dNTP), an inverted primer solution, and the nucleic acid synthetase solution are sequentially applied to the substrate for nucleic acid amplification 401, on which primers are previously fixed, from the solution sending unit 405, through the inlet 714 and the flow channel 404. After the temperature of the thermoregulating plate 403 is increased to 37° C., the temperature is retained constant for a given time period to perform complementary strand synthesis using the primers fixed on the base material as starting points; the retention time is preferably three to ten minutes. Next, after the temperature of the thermoregulating plate 403 is increased to 60° C., DNA amplification reaction is induced. The reaction time is preferably two to seven hours. After the DNA amplification reaction, the washings for rinsing away and removing the unreacted components and the complementary strands of the products from extension reaction are applied from the solution sending unit 405 through the inlet 714 and the flow channel 404.

Next, sequencing reaction is induced to repeat single nucleotide extension reaction and fluorescence detection. To induce the sequencing reaction, for example when a serial reaction mode is used, the fluorescently-labelled nucleotide may be used, in which a 3'-O-aryl group is incorporated in the position 3' OH of ribose as a protective group, as disclosed in the nonpatent literature 4 and a fluorochrome is coupled to the position 5 of pyrimidine, or the position 7 of purine through an aryl group. The aryl group is cut away when being exposed to irradiated light (for example wavelength 355 nm) or coming into contact with palladium, achieving both extinction of the fluorochrome and control over the extension reaction.

Fluorescence measurement is performed as described below. It is preferable that a xenon lamp is used for a light source 407 in terms of the need for excitation of many types of fluorescent substances and economic efficiency. After a collimator lens 408 is used to adjust so that the parallel light is irradiated, near-ultraviolet light, which is unnecessary for excitation and may damage the fluorochrome, is eliminated with a filter 713, and the light is introduced into an objective lens 406 using a dichroic mirror 409 and irradiated on the substrate for nucleic acid amplification 401. The fluorescence beams emitted from fluorochrome molecules labelled on the individual bases pass inversely through the same coaxial light path as an excitation light and collected at the objective lens 406, pass through the dichroic mirror 409, and form an image on the photosensitive surface of a two-dimensional CCD camera 712 through an imaging lens 711. Scattering light is removed from the excitation light through an optical filter 710. To identify four types of bases, the fluorescence beams from four kinds of fluorochromes need to be independently identified; one of the methods for observation is that the dichroic mirrors 409, which have wavelength characteristics suitable to these four types of fluorochromes, are used and they are supported by individual rotary mirror holders to rotate at appropriate angles to switch between the wavelengths (fluorochromes) to be measured.

As shown above, by fabricating the apparatus for nucleic acid analysis with the solution sending unit, the thermoregulating plate, an excitation light source, and the fluorescence detection unit incorporated therein, the process, ranging from sequencing reaction to measurement, may be automatically performed based on the amplification reaction on the base material of DNA samples, considerably improving the throughput compared with those of the conventional techniques.

The number of fluorescent molecules necessary for detecting the sequencing reaction at the signal/noise ratio of 10 or more was obtained using the fluorescent beads (Fluosphere (R) beads from Invitrogen Corporation, 200 nm in diameter, containing fluorescent molecules $1.1 \times 10^5$), in which the number of contained fluorescent molecules has been known, with respect to the number of DNA molecules per cluster. The result showed that $1 \times 10^4$ molecules are required. For this reason, to detect the sequencing reaction at the signal/noise ratio of 10 or more, at least 10,000 molecules per cluster need to be synthesized, demonstrating that the amplification factor of 10,000-fold or more is preferable.

As described in reference to the example 1, the method for nucleic acid amplification achieves 10,000 DNA fragments per cluster, demonstrating that the sequencing reaction may be detected at the signal/noise ratio of 10 or more.

Example 5

Figure 5:
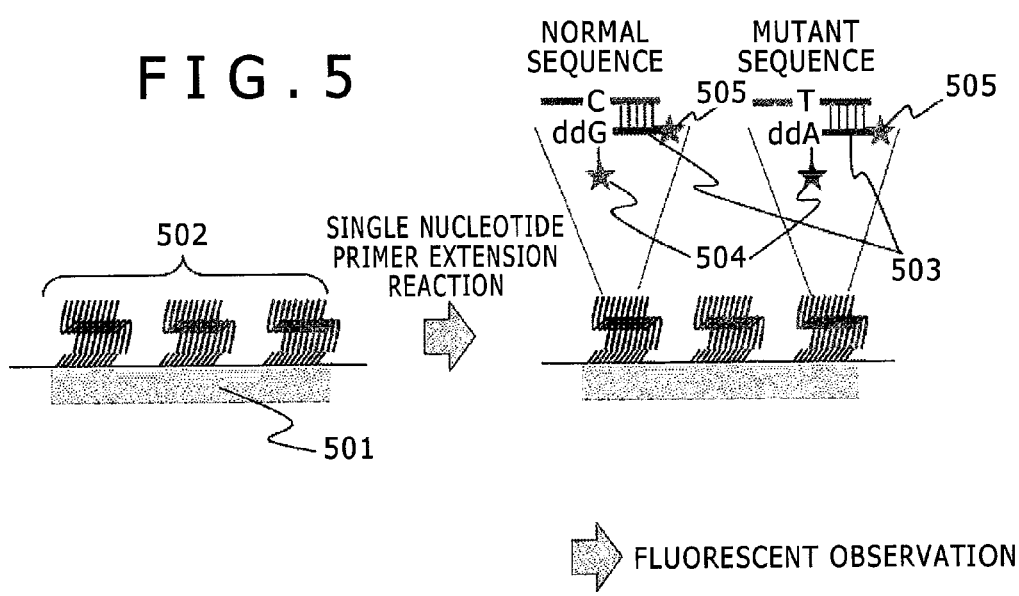
FIG. 5 is a view of an example of the method for nucleic acid analysis of the present invention.

By reference to an example 5, an example of the method for nucleic acid analysis using the method for nucleic acid amplification of the present invention using FIG. 5. The method, in particular, is disclosed for obtaining accurately the abundance ratio between abnormal sequence fragments with a mutation in the specific position and normal sequence fragments with no mutation. The method for nucleic acid amplification of the present invention enables fragmented DNA samples to be fixed in the different positions on the substrate one by one for amplification, making it possible to easily detect any mutation in the specific position contained in the samples for analyzing its abundance ratio.

Using the method described in reference to the example 1, clusters 502 of nucleic acid sample fragments to be analyzed is formed on a smooth substrate 501. Next, primers 503 having the base sequence up to the position adjacent to the position of a target mutation are applied to the clusters 502 of nucleic acid sample fragments for hybridization. The end of primer 503 has been previously modified with a fluorochrome 505. Next, a dideoxynucleotide solution containing the fluorochromes specific to the individual base types is applied and DNA synthetase is added to induce the extension reaction. As known from FIG. 5, dideoxyguanine (ddG) has been incorporated in the normal sequence, causing the extension reaction to stop, while, dideoxyadenine (ddA) has been incorporated in the abnormal sequence, causing the extension reaction to stop. For example, dideoxyguanine has been Cy3-labelled and dideoxyadenine has been Cy5-labelled. Next, an exciting light is irradiated onto the smooth substrate 501 under the standard fluorescent microscope to observe fluorescence. Whether the sample fragments contain the base sequence, in which any mutation is analyzed, may be determined based on the existence or absence of the fluorochrome 505. The number of luminescent points of the fluorochrome 505, where Cy3 fluorescence is emitted, and the number of luminescent points of the fluorochrome 505, where Cy5 fluorescence is emitted, are obtained. The ratio between these results is calculate, making it possible to accurately the ratio between the normal and abnormal sequences contained in the DNA samples.

LIST OF REFERENCE SIGNS

101, 301 DNA sample
102 Bulky DNA molecule
103 Base material
104, 205 Primer DNA
105 Inverted primer DNA
106 Product from extension reaction
201 Support base material
202 Positive photoresist for electron beam
203 Adhesive pad
204 Functional group
206 Non-specific adsorption preventive film
302 Fragment
303 Adaptor
304 Linker for circle formation
305 Circular DNA
306 Primer DNA
307 RCA product
401 Substrate for nucleic acid amplification
402 Member for flow channel formation
403 Thermo-regulating plate
404 Flow channel
405 Solution sending unit
406 Objective lens
407 Light source
408 Collimator lens
409 Dichroic mirror
410, 413 Optical filter
411 Imaging lens
412 Two-dimensional CDD camera

The invention claimed is:

1. A method for nucleic acid amplification comprising:
arranging regions with first nucleic acid fragments fixed therein at a fixation density of at least 10,000 molecules/$\mu m^2$ and regions without the first nucleic acid fragments fixed therein in a pattern on a surface of a base material;
fixing second nucleic acid fragments as a template, each having at least two or more base sequences to be analyzed on a same chain, to the regions with the first nucleic acid fragments, where each one of the second nucleic acid fragments is fixed to one of the regions with the first nucleic acid fragments; and
inducing an amplification reaction on the second nucleic acid fragments to amplify the base sequences at least 10,000-fold,
wherein the second nucleic acid fragments are single-stranded and have a self-annealing structure.

2. A method for nucleic acid amplification comprising:
arranging regions with first nucleic acid fragments fixed therein at a fixation density of at least 10,000 molecules/$\mu m^2$ and regions without the first nucleic acid fragments fixed therein in a pattern on a surface of a base material;
fixing second nucleic acid fragments as a template, each having at least two or more base sequences to be analyzed on a same chain, to the regions with the first nucleic acid fragments, where each one of the second nucleic acid fragments is fixed to one of the regions with the first nucleic acid fragments; and
applying third nucleic acid fragments to induce an amplification reaction on the second nucleic acid fragments to amplify the base sequences at least 10,000-fold using the first and third nucleic acid fragments as primers,
wherein the second nucleic acid fragments are single-stranded and have a self-annealing structure.

3. The method for nucleic acid amplification according to claim 1, wherein an average value of diameters of the second nucleic acid fragments is larger than one-half of an average value of diameters of the regions with the first nucleic acid fragments fixed therein.

4. The method for nucleic acid amplification according to claim 1, further comprising:
   removing a complementary strand of products from an extension reaction on the first nucleic acid fragments after the amplification reaction.

5. The method for nucleic acid amplification according to claim 1, wherein the second nucleic acid fragments are products from an extension reaction with a strand displacement reaction in the presence of a polymerase having strand displacement activity using circular nucleic acid fragments having the base sequences to be analyzed as a template.

6. The method for nucleic acid amplification according to claim 1, wherein the amplification reaction is an isothermal reaction.

7. The method for nucleic acid amplification according to claim 1, wherein an average value of diameters of the regions with the first nucleic acid fragments fixed therein is equal to or less than 500 nm.

8. The method for nucleic acid amplification according to claim 1, wherein the fixation density is 100,000 molecules/ $\mu m^2$ or more.

9. The method for nucleic acid amplification according to claim 1, wherein a reaction temperature for the amplification reaction is between 50 to 70° C.

10. The method for nucleic acid amplification according to claim 1, wherein the second nucleic acid fragments are bulky nucleic acid fragments synthesized through a Rolling Circle Amplification (RCA) reaction.

11. A method for nucleic acid analysis further comprising:
   inducing an extension reaction for capturing fluorescently-labeled bases after the method for nucleic acid amplification according to claim 1 has been performed; and
   detecting fluorescence of the fluorescent labeled bases.

12. A method for nucleic acid analysis further comprising:
   inducing an extension reaction for capturing fluorescently-labeled bases after the method for nucleic acid amplification according to claim 2 has been performed; and
   detecting fluorescence of the fluorescent labeled bases.

13. The method for nucleic acid amplification according to claim 1, wherein the fixation density is 50,000 molecules/ $\mu m^2$ or more.

14. The method for nucleic acid amplification according to claim 2, wherein the fixation density is 50,000 molecules/ $\mu m^2$ or more.

* * * * *

SEQUENCE LISTING

```
<160> NUMBER OF SEQ ID NOS: 4

<210> SEQ ID NO 1
<211> LENGTH: 526
<212> TYPE: DNA
<213> ORGANISM: Artificial Sequence
<220> FEATURE:
<223> OTHER INFORMATION: Description of Artificial Sequence: Synthetic
      circular polynucleotide modified from
      expression vector pSPT19

<400> SEQUENCE: 1
ctagcgatga ccctgctgat tggttcgctg accatttccg ggtgcgggac ggcgttacca        60
gaaactcaga aggttcgtcc aaccaaaccg actctgacgg cagtttacga gagagatgat      120
agggtctgct tcagtaagcc agatgctaca caattaggct tgtacatatt gtcgttagaa      180
```

```
cgcggctaca attaatacat aaccttatgt atcatacaca tacgatttag gtgacactat    240
agaatacacg gaattcgagc tcggtacccg ggatcattgg atcctaatac gactcactat    300
agcaatggta cggtacttcc tataacgccc gtgttgctcg gttatcaaaa gtgcacgcta    360
ctttgctaaa agcttatgga taagcttggg tctccctata gtgagtcgta ttaatttcga    420
taagccagct gggcctcgcg cgtttcggtg atgacggtga aaacctctga cacatgcagc    480
tcccggagac ggtcactggc cgtcgtttta cgctagcatc ggatcg                   526

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-end modified with thiol

<400> SEQUENCE: 2
taatacgact cactatagg                                                  19

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
actggccgtc gttttac                                                    17

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-end modified with Cy3

<400> SEQUENCE: 4
ctatagtgtc acctaaatcg tatg                                            24
```